United States Patent [19]

Lee

[11] 4,242,087
[45] Dec. 30, 1980

[54] ARTICULATOR YOKE ASSEMBLY

[76] Inventor: Robert L. Lee, 22937 Grand Ter., Colton, Calif. 92324

[21] Appl. No.: 964,979

[22] Filed: Nov. 30, 1978

[51] Int. Cl.³ .............................................. A61C 11/00
[52] U.S. Cl. ......................................... 433/54; 433/68
[58] Field of Search ................... 32/32, 20; 433/54, 68

[56] References Cited

U.S. PATENT DOCUMENTS

| 1,055,718 | 3/1913 | Davis et al. | 32/32 |
| 1,550,339 | 8/1925 | Branson et al. | 32/32 |
| 1,753,965 | 4/1930 | Ralph | 32/32 |
| 3,052,030 | 9/1962 | Spence | 32/32 |
| 3,206,852 | 9/1965 | Swanson | 32/32 |
| 3,350,782 | 11/1967 | Guichet | 32/32 |
| 3,896,550 | 7/1975 | Lee | 32/32 |
| 4,034,474 | 7/1977 | Lee | 433/68 |
| 4,045,872 | 9/1977 | Arant | 32/32 |

Primary Examiner—Louis G. Mancene
Assistant Examiner—John J. Wilson
Attorney, Agent, or Firm—Knobbe, Martens, Olson, Hubbard & Bear

[57] ABSTRACT

A mounting device for use in mounting a dental cast of a patient's maxillary teeth in a dental articulator including a removable yoke like bracket for mounting a face bow on the articulator.

14 Claims, 6 Drawing Figures

ARTICULATOR YOKE ASSEMBLY

BACKGROUND OF THE INVENTION

The present invention relates to a device used in conjunction with a reference plane device to accurately mount a cast of a patient's teeth on a dental articulator.

The purpose of a dental articulator is to stimulate the jaw or condylar movements of a patient. This instrument enables a dentist to obtain the necessary diagnostic information for the treatment of occlusal irregularities, such as malocclusion, and the fabrication of dental casts or dentures.

In a human, the lower jaw or mandible moves both laterally and vertically with respect to the upper jaw or maxilla. The mandible is hinged to the maxilla by means of two temporomandibular joints which are found on the sides of the head of a person near the ears. This joint consists of a condyle, which is part of the mandible, and which moves in a ball-and-socket-type joint and is joined to the maxilla by human cartilage and other tissue. A line running between a person's temporomandibular joints would define an imaginary "hinge axis" about which the mandible would rotate with respect to the maxilla.

A dental articulator consists of a lower frame and upper frame which move relative to each other so as to simulate the movement of the human mandible relative to the maxilla. In the case of the articulator, however, the upper frame or maxilla is moved relative to the lower frame or mandible, while in a human, the reverse is true. Nonetheless, it has been found that this fact makes no difference with respect to occlusal analysis. The hinging action of the articulator is accomplished by means of a pair of guide blocks which are mounted in the upper frame and which have openings on their lower surfaces to receive a pair of styluses correspondingly mounted on the lower frame. The styluses generally represent the human condyles and provide a hinge axis about which the upper frame can rotate and move. The hinge axis in the articulator, which corresponds to a patient's hinge axis, is a line through the centers of the styluses.

In U.S. Pat. No. 3,452,493, issued to Robert L. Lee on July 1, 1969, there is described a system of jaw movement simulation wherein the dynamic movement of the patient's jaws is reported and from this information, plastic guide blocks are formed. In U.S. Pat. Nos. 4,034,474 and 4,034,475, both issued to Robert L. Lee on July 12, 1977, there is suggested that plastic guide blocks of the type disclosed in the earlier Lee patent be classified according to certain characteristics of jaw movements to provide a series of average value blocks from which the pair most closely fitting the measurements of a particular patient's condylar movements may be selected. Further examples of such a system are disclosed in U.S. patent application, Ser. No. 814,815 which is pending. These blocks have three dimensional openings or pathways cut therein which receive a stylus, thus enabling a dentist to treat accurately an occlusal or denture problem without requiring the presence of the patient.

In order to efficiently utilize the articulator in simulating the jaw movements of a particular patient, it is not enough to simply select the proper pair of guide blocks. It is also just as important that the dental casts of the patient's maxillary and mandibular teeth be accurately mounted in the articulator so that their relative position is the same as they would be in the patient's mouth. The mounting device of the present invention is utilized in conjunction with the articulator and a face bow which establishes the location of the patient's hinge axis with respect to a reference plane, and is used for accurately mounting the dental casts on the articulator.

It is convenient to support the upper frame of an articulator on the lower frame while mounting a dental cast to the upper frame. However, the styluses on the lower frame forming a hinge axis tend to interfere with the operation unless they are conveniently laterally adjustable. In some prior art arrangements the styluses must be removed and cumbersome auxiliary equipment is required for transferring face bow reference plane information to the articulator.

In the system of the above-referenced Lee patents, it has been found desirable to have the styluses on the articulator spaced a fixed distance. Greater accuracy and consistency can be attained with fixed styluses and it has been found unnecessary that the styluses be spaced a distance equal to the spacing of the patient's condyles. However, the face bow used in locating the patient's condylar hinge axis must be adjustable in width to engage th patient's head against the tempromandibular joints. Thus, it is desirable that means be provided for easily transferring the face bow information to a fixed stylus articulator and other articulators in which it is not convenient to laterally adjust the styluses.

SUMMARY OF THE INVENTION

The present invention consists of an assembly which is mounted on a dental articulator and used in conjunction with a reference plane device in accurately mounting a cast of a patient's maxillary teeth in the articulator. Once the maxillary cast is properly mounted, a cast of mandibular teeth can be properly positioned relative to the maxillary teeth using conventional occlusal techniques.

The mounting device of the present invention includes a yoke or mounting bracket which is attached to the vertical portion of the lower frame of an articulator. Two supports are attached to the bracket having holes defining an axis spaced from the hinge axis on the lower frame so as not to interfere with the styluses forming the hinge axis. Extending through the holes in the supports are two hinge axis extension pins which are inserted into guide block mounting holes in the rear portion of the upper frame of an articulator. At the outer end of each extension pin is found an adapter device or other means having a small dimple or other attachment means for cooperating with tips of a face bow utilized in locating a reference plane on the patient's face.

In the above-referenced U.S. Pat. No. 4,034,474, there is disclosed an analyzer system for obtaining jaw movement information useful in selecting a pair of guide blocks to be mounted on the dental articulators for controlling movement of the articulator. Included in the analyzer system is the measurement and the recording of mandibular movement relative to a reference plane. The reference plane is defined by three points. The first two of these reference points are located near the ears of the patient and define the hinge axis about which that particular patient's mandible tends to rotate with respect to the maxilla. The third reference point is found at an arbitrary site on the side of the patient's nose.

In preparation for positioning the dental casts in the articulator, a face bow is placed on the patient's head and used to prepare a bitepiece while again registering with three points of the reference plane established earlier by the analyzer system.

The upper frame of the articulator is then removed from the lower frame and the mounting bracket of the invention is attached to the vertical portion of the lower frame. The guide blocks are removed from the upper frame, and the hinge axis extension pins of the mounting device are placed through the holes in supports attached to the bracket and into the mounting holes in the upper frame in which the guide blocks are normally mounted. The support holes are positioned so as not to interfere with the lower from styluses. This is advantageous in that with some prior art arrangements it is necessary to move the styluses which includes potential error to the system.

The hinge axis extension pins are laterally adjusted so that the facebow tips, with the bite piece attached, are placed into dimples on the adapters at the end of the extension pins, and the reference plane properly positioned. With the facebow in this position, the maxillary dental cast can then be inserted into the bite piece; and while supported there, it is plastered to the mounting area of the upper frame. The facebow can then be removed as can the yoke assembly. The desired guide blocks may be mounted on the articulator through pins extending into the holes formerly occupied by the extension pins of the yoke assembly. The mandibular dental cast can be mounted on the lower frame and the articulator used according to conventional occlusal techniques.

Thus, the yoke assembly of the present invention enables the articulator to receive the facebow information and thereby establish the all important reference plane for the accurate positioning of the maxillary dental cast in the articulator.

These and other advantages of the present invention are readily apparent upon reference to the drawings in which.

DETAILED DESCRIPTION OF THE PREFERRED EMBODIMENT

Figure 1:
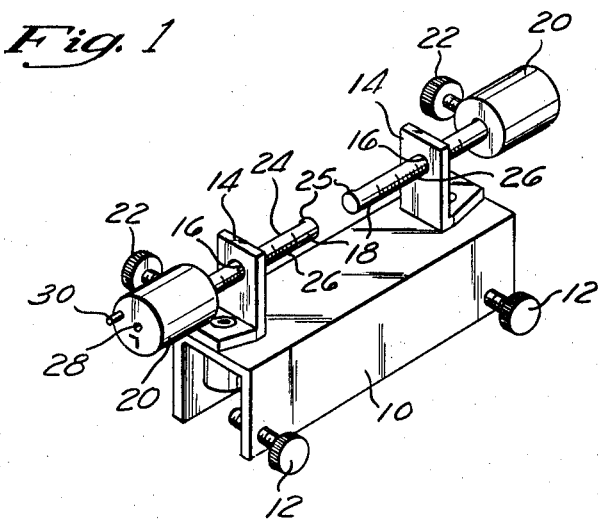
FIG. 1 is a perspective view of the mounting device of the present invention, showing the yoke and the assembly thereof.

Referring to FIG. 1, there is shown the mounting device of the present invention, including a generally U-shaped yoke or bracket 10 which is placed over the vertical portion of the lower frame of a dental articulator and fixed thereon by means of set screws 12. Extending up from the yoke are vertical supports 14 which have guide holes 16 therein.

Hinge axis extension pins 18 are inserted through the guide holes. A barrel-shaped adapter 20 is slideably mounted on each pin and can be fixed thereto by a set screw 22. The extension pins have graduation markings 26, which are useful in positioning the pins within the guide block mounting holes of the upper frame of the articulator. Found on the outer end surfaces of the adapters are a pair of dimples 28 which receive hinge axis pointers of a facebow. Also found on that surface are adapter pins 30 which are useful in receiving facebows of a type other than that having hinge axis pointers, such as those disclosed in the present application.

Figure 1A:
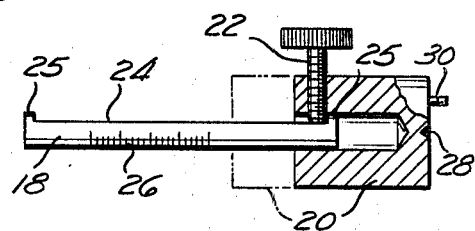
FIG. 1a is a cross-sectional view showing the flattened surface of the extension pins and the two positions of the adapter relative thereto.

Shown in FIG. 1a is a cross-sectional view of a single hinge axis extension pin showing that it has a flattened surface 24 which extends longitudinally along the length of the pin except for shoulders 25 at each end. A set screw 22 bears against the surface 24. Also shown are the two positions of adapters 20 along the extension pins 18. As shown in solid lines, the outermost position occurs when set screw 22 engage shoulder 25 and prevents further removal of the adapter. The inner most position is shown in dotted lines and occurs when the end of the adapter abuts shoulder 25. Ring lines on the pins 14 also mark the limits of movement of the adaptors 20.

PROCEDURE

As described in detail in U.S. Pat. No. 4,034,474, an analyzer system is used to measure and record mandibular movement relative to a reference plane defined by three points. The first two of these reference points are located near the ears of the patient and define that particular patient's hinge axis. The third reference point is arbitrarily located on the side of the patient's nose. At each of these three reference points, small marks are made on the patient's skin so that they can be later located.

Figure 2:
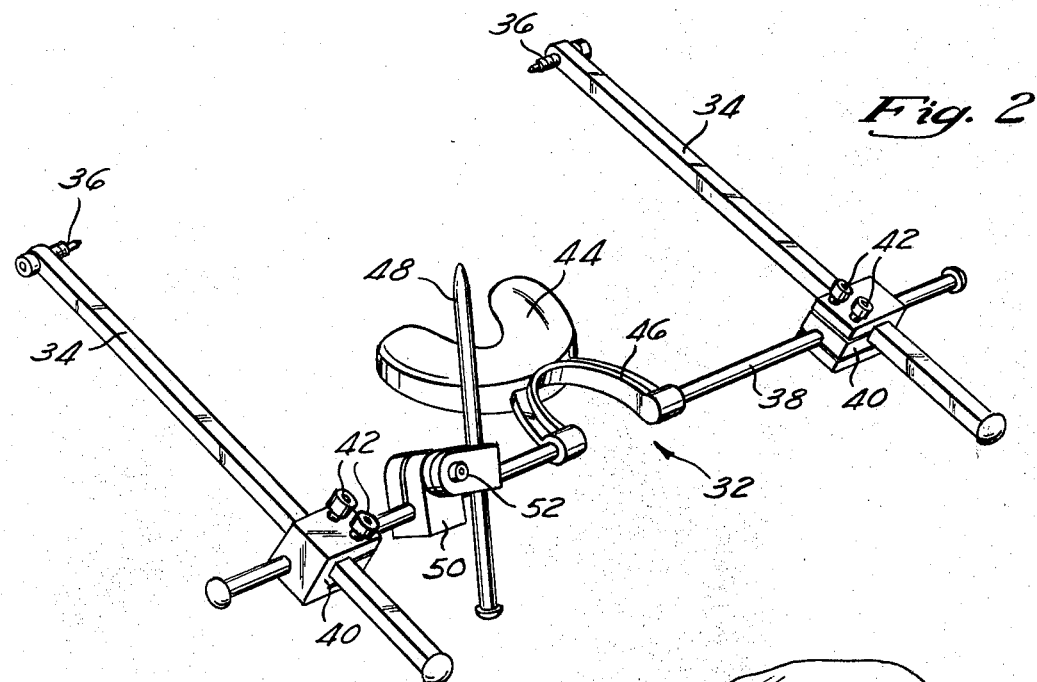
FIG. 2 is a perspective view of the facebow showing the three pointers which establish the reference plane.

A facebow 32, such as that illustrated in FIG. 2, is utilized to prepare a bitepiece for the patient's maxillary teeth in preparation for mounting of a maxillary dental cast in an articulator. The facebow 32 consists of two parallel side arms 34 with two hinge axis pointers 36 located at the rear of the side arms and oriented perpendicular thereto. A transverse rod 38 is adjustably connected to side arms 34 and also oriented perpendicular thereto by means of suitable clamps 40. The transverse rod can be fixed relative to the side arms by tightening screws 42. Positioned near the middle of the transverse rod is a bitefork 44 attached to the rod by means of a bridge 46. Also attached to the rod near one of the side arms is nose pointer 48 which is slidably attached to the rod 38 by means of a suitable adjustable clamp 50.

Figure 2A:
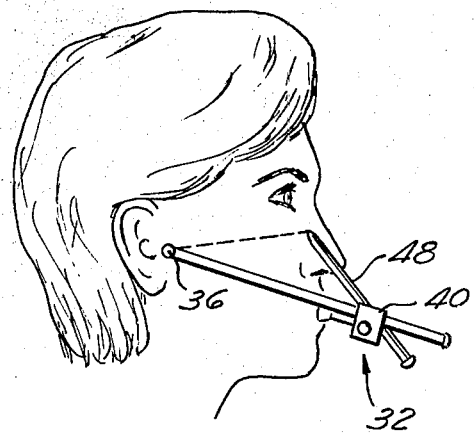
FIG. 2a is a side view of the patient's head showing the manner in which the facebow is applied.

A quantity of pre-heated modeling compound is placed on the bitefork 44, and placed in the patient's mouth with the facebow attached to the patient's head in the manner shown in FIG. 2a. The patient bites into the modeling compound, thus leaving an impression therein. While the patient holds the bite piece between the teeth the compound is allowed to harden. Once hardened, the hinge axis pointers 36 are precisely aligned on the hinge axis points overlying the temporomandibular joints near the ears of the patient, and the nose pointer 48 is placed on the nose reference point, as shown in FIG. 2a. Screws 42 on the side arms and screw 52 on the swivel joint are then tightened so that the facebow is maintained rigidly in the position shown in FIG. 2a.

Figure 3:
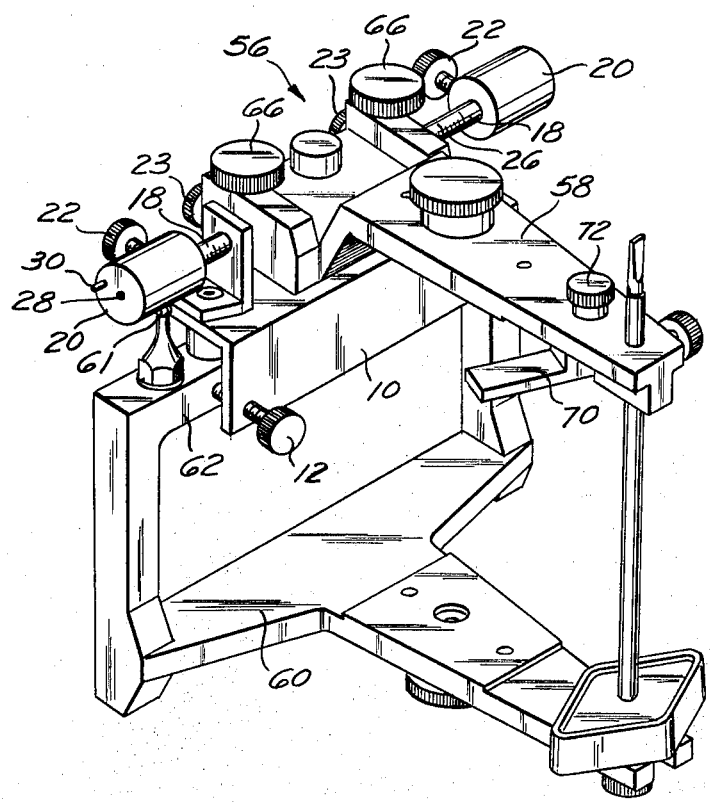
FIG. 3 is a perspective view of the mounting device attached to the articulator.

The mounting device of the present invention is attached to the articulator 56, as shown in FIG. 3, by first, separating the upper frame 58 from the lower frame 60. The yoke 10 is then mounted on the vertical portion 62 of the lower frame by means of set screws 12. Note that the pins 18 are above the styluses 61. The guide blocks (not shown) of the upper frame are removed and the upper frame 58 is placed on the lower frame in the position shown in FIG. 3. The hinge axis extension pins 18 are then placed through the guide holes 16 of the vertical supports 14 and into mating guide block mounting holes (not shown) in the vertical sides of the rear portion of the upper frame.

Figure 4:
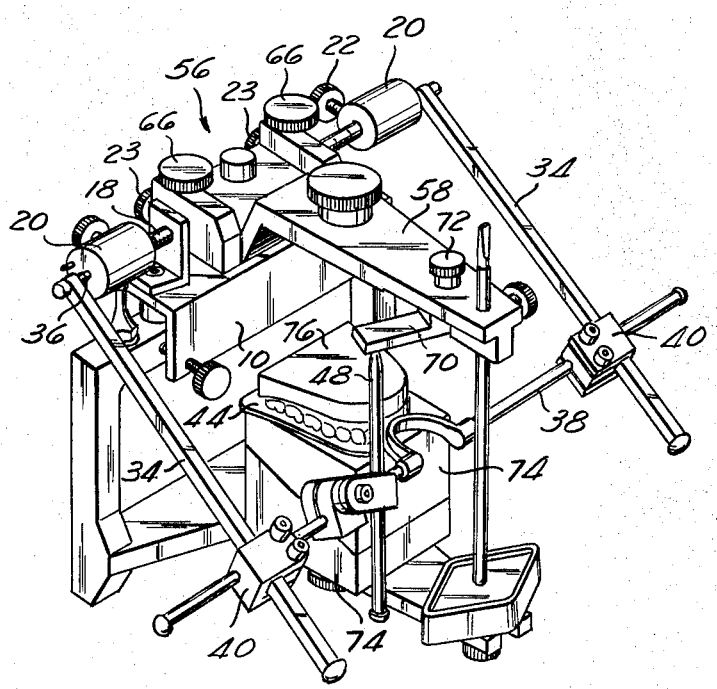
FIG. 4 is a perspective view of the mounting device on the articulator with the facebow attached, thus registering the position of the reference plane and enabling the maxillary dental cast to be accurately positioned in the articulator.

The articulator and mounting device assembly is now prepared to receive the facebow and bite piece assembly, as shown in FIG. 4. If the patient has a wide head, the adapters 20 are moved to their outermost position and fixed there by set screws 22, as shown in solid lines in FIG. 1a. If the patient's head is sufficiently narrow, the adapters are fixed in their innermost position, which is shown in dotted lines in FIG. 1a. Secondly, the width of the hinge axis extension pins is adjusted so that the hinge axis pointers 36 of the face bow will fit securely into dimples 28 on the adapters. This is accomplished by laterally adjusting the extension pins 18 within the upper frame 58 of the articulator to the proper width, positioning them to equal depths within the upper frame by using graduated markings 26, and tightening set screws 66. The hinge axis pointers of the facebow are then inserted into the dimples in the adapters and the face bow is allowed to rest upon the table or desk.

The reference plane indicator 70 found on the upper frame of the articulator is adjusted by loosening screw 72 and then tightening it again after the reference plane indicator is positioned at an angle extending away from the upper frame, as shown in FIG. 4. The nose pointer 48 of the facebow is then elevated to a point where it is just touching the reference plane indicator 70. The facebow is supported in this position by wedge blocks 74. A dental cast 76 of the patient's maxillary teeth is placed into the bite piece compound on the bite fork 44. The maxillary cast is then plastered to the upper frame while held in this position. The maxillary cast is thus attached to the upper frame of the articulator with respect to the same three point reference plane which was earlier located on the head of the patient, thereby enabling the simulation of the patient's jaw movements by the articulator.

For mounting a mandibular cast, the axis extension pins 18 are removed from the upper frame 58 and replaced by the appropriate guide blocks (not shown) for receiving the styluses 61. The two frames are then joined by locking the styluses in the guide blocks in centric position, as further explained in the above-referenced patents.

Next, the articulator is turned upside down and the patient's centric relations record (not shown) is placed on the maxillary teeth. This record is one which should have been obtained earlier from examination of the patient and which accurately depicts the location of the mandibular teeth with respect to the maxillary teeth. With the centric relations record on the maxillary teeth, a dental cast of the mandibular teeth can then be placed over the record and accurately positioned relative to the maxillary cast. The mandibular cast is then plastered to the other frame of the articulator while maintaining this accurate relationship. When the plaster has set, the articulator can be opened and the centric relations record removed. The casts of the maxillary and mandibular teeth are now mounted in the articulator in a position which will allow the accurate simulation of the patient's jaw movements by the articulator.

If a facebow which will require the use of adapter pins 30 is to be used in this mounting procedure, it is important set screws 22 and a pair of set screws 23 located at the rear of upper frame 58 engage the flattened surface of extension pins 18. This will insure that the adapter pins are properly positioned for receipt of the face bow.

What is claimed is:

1. In a dental articulator including a lower frame having a horizontal portion with a mounting area thereon to receive a dental cast and having a vertical portion with an upper surface, an upper frame having a forward portion with a mounting area thereon and a rear portion with guide blocks removeably mounted in mounting holes in said rear portion, said articulator further having a pair or styluses mounted on said upper surface of said vertical portion for communication with said guide blocks, a mounting device for accurately positioning a facebow on the upper frame as an aid to mount a dental cast on the upper frame comprising:

a bracket adapted to be removeably mounted on said lower frame;

a pair of guide supports mounted on said bracket; and hinge axis extension means supported by said guide supports to be fixed at a location not to interfere with said styluses and fixed within said holes in said rear portion of said upper frame when said guide blocks are removed, said extension means having at their outer opposite ends means for attachment to said facebow.

2. The mounting device of claim 1 wherein said hinge axis extension means includes a pair of extension pins having adapters at their outer ends which are laterally adjustable relative to said pins, and wherein said means for attachment are dimples in said adapters.

3. The mounting device of claim 2 wherein said extension pins have graduated markings to assist in determining the position at which they are to be fixed within said rear portion holes.

4. The mounting device of claim 1 including a pair of small pins mounted on said ends suitable for adapting said mounting device for use with a facebow having means for cooperating with said small pins.

5. The mounting device of claim 4 wherein said extension means includes a pair of extension pins each having a flat side for use in orienting said small pins properly.

6. The device of claim 1 wherein said guide supports extend upwardly from said articulator lower frame whereby said extension means are located above said styluses.

7. The device of claim 6 wherein said bracket is located between said styluses.

8. Dental apparatus comprising:

a dental articulator lower frame having a horizontal portion with a mounting area thereon to receive dental casts and a vertical portion with an upper surface having styluses attached thereto defining a hinge axis;

a dental articulator upper frame having a forward portion with a mounting area thereon and having a rear portion with one or more transverse mounting holes thereon for removeably supporting a pair of guide blocks which cooperate with said styluses when using the articulator;

a pair of hinge axis extension pin means supported by said lower frame vertical portion and fixed within said mounting holes of said rear portion of said upper frame when said guide blocks are not being supported by said holes, to thereby support the upper frame rear portion on an axis spaced from said styluses, said pin means having means at their outer opposite ends to receive hinge axis pointers of a device which fixes the location of the patient's maxillary teeth with respect to a reference plane.

9. The apparatus of claim 8 including a bracket mounted on said lower frame, and a pair of uprights attached to said bracket with axially aligned holes therein, and with said pin means extending therethrough, said holes being out of alignment with said styluses so that said pin means do not interfere with said styluses.

10. A mounting device for a dental articulator, comprising:

a yoke-like bracket adapted to be removeably mounted on the rear vertical portion of a lower frame of said articulator to assist in mounting dental casts to the articulator;

a pair of uprights attached to said bracket with axially aligned holes therein;

a pair of hinge axis extension pins inserted into said holes in said uprights;

a pair of adapters mounted for slidable, lateral adjustment on said extension pins, each of said adapters having means on its outer end for cooperating with tips of a dental facebow.

11. The device of claim 10 wherein said pins have a flat surface extending longitudinally along the exterior of said pins; and said adapters are fixed with respect to said pins by a set screw engaging said flat surface; said means on the outer ends of said adapters is a centrally located dimple and including a reference element on the outer end of each adapter and spaced radially from said dimple for cooperating with a different type of face bow, said pin flat surface being oriented with respect to said reference element to orient properly said reference element.

12. The device of claim 10 wherein said bracket has a generally U-shaped cross-section which fits over said lower frame vertical portion and is sized to fit between a pair of styluses extending upwardly from the frame and defining a hinge axis for the frame, and wherein said holes define an axis which is spaced from said hinge axis sufficiently so that said pins do not interfere with said styluses.

13. A method of transferring a maxillary dental cast to the upper frame of a dental articulator having guide blocks comprising:

Temporarily removing said guide blocks

Temporarily mounting supports on the lower frame of said positioning extension pin means on said supports and temporarily mounting said pins in the rear portion of an upper frame of the articulator at a location normally occupied by said guide blocks of the upper frame, said supports and pin extension means being located so as not to interfere with the means on the lower frame of the articulator defining a hinge axis for the articulator which cooperates with the guide blocks during use of the articulator;

aligning the tips of a face bow with means on the outer ends of said pin means;

aligning a nose pointer attached to said face bow with a reference point on said upper frame and thus locating a dental cast supported by a bitepiece attached to said face bow; and attaching said dental cast to said upper frame while the cast is located on said bitepiece.

14. The method of claim 13 wherein said supports are mounted on the upper surface of the lower frame and extend upwardly sufficiently so that said extension pins are located above the means defining said hinge axis.

* * * * *

UNITED STATES PATENT AND TRADEMARK OFFICE
CERTIFICATE OF CORRECTION

PATENT NO. : 4,242,087
DATED : December 30, 1980
INVENTOR(S) : Robert L. Lee

It is certified that error appears in the above—identified patent and that said Letters Patent are hereby corrected as shown below:

Column 8, line 18, after "said", --articulator-- should be inserted.

Signed and Sealed this

Fourteenth Day of July 1981

[SEAL]

Attest:

Attesting Officer

GERALD J. MOSSINGHOFF

Commissioner of Patents and Trademarks